(12) United States Patent
Hamamoto et al.

(10) Patent No.: US 8,323,693 B2
(45) Date of Patent: Dec. 4, 2012

(54) EXTERNAL PREPARATION FOR WOUNDS

(75) Inventors: Hidetoshi Hamamoto, Kitajima-cho (JP); Keiko Yamasaki, Higashikagawa (JP); Hideakira Yokoyama, Tokushima (JP); Akihiko Hirata, Naruto (JP); Takeru Fujii, Naruto (JP)

(73) Assignees: Medrx Co., Ltd., Kagawa (JP); Nippon Shinyaku Co., Ltd., Kyoto (JP)

( * ) Notice: Subject to any disclaimer, the term of this patent is extended or adjusted under 35 U.S.C. 154(b) by 1174 days.

(21) Appl. No.: 10/507,522

(22) PCT Filed: Mar. 12, 2003

(86) PCT No.: PCT/JP03/02887
§ 371 (c)(1),
(2), (4) Date: Sep. 14, 2004

(87) PCT Pub. No.: WO03/075886
PCT Pub. Date: Sep. 18, 2003

(65) Prior Publication Data
US 2005/0118269 A1    Jun. 2, 2005

(30) Foreign Application Priority Data

Mar. 14, 2002 (JP) ................................ 2002-069901
Apr. 23, 2002 (JP) ................................ 2002-120084
Jun. 28, 2002 (JP) ................................ 2002-189912

(51) Int. Cl.
*A61K 9/14* (2006.01)
(52) U.S. Cl. ...... 424/484; 424/485; 424/487; 424/78.06
(58) Field of Classification Search ............... 424/445
See application file for complete search history.

(56) References Cited

U.S. PATENT DOCUMENTS

| | | | |
|---|---|---|---|
| 4,124,748 A * | 11/1978 | Fujimoto et al. | 525/60 |
| 4,374,126 A | 2/1983 | Cardarelli et al. | |
| 4,401,651 A * | 8/1983 | Knutson | 424/78.06 |
| 4,526,938 A | 7/1985 | Churchill et al. | |
| 4,554,156 A | 11/1985 | Fischer et al. | |
| 4,615,697 A | 10/1986 | Robinson | |
| 4,647,636 A * | 3/1987 | Makita et al. | 526/206 |
| 4,746,509 A | 5/1988 | Haggiage et al. | |
| 4,771,105 A * | 9/1988 | Shirai et al. | 525/54.23 |
| 4,830,855 A | 5/1989 | Stewart | |
| 4,942,035 A | 7/1990 | Churchill et al. | |
| 4,954,562 A * | 9/1990 | Anderson | 524/779 |
| 4,959,341 A | 9/1990 | Wallach | |
| 5,061,700 A * | 10/1991 | Dow et al. | 514/169 |
| 5,336,501 A * | 8/1994 | Czech et al. | 424/445 |
| 5,362,497 A * | 11/1994 | Yamada et al. | 424/449 |
| 5,618,799 A | 4/1997 | Inagi et al. | |
| 5,626,866 A | 5/1997 | Ebert et al. | |
| 5,693,034 A | 12/1997 | Buscemi et al. | |
| 5,712,316 A | 1/1998 | Dahmen et al. | |
| 5,730,999 A | 3/1998 | Lehmann et al. | |
| 6,268,355 B1 * | 7/2001 | Mizobuchi et al. | 514/165 |
| 6,391,294 B1 | 5/2002 | Dettmar et al. | |

FOREIGN PATENT DOCUMENTS

| | | |
|---|---|---|
| EP | 0 092 918 | 11/1983 |
| EP | 0 123 585 | 10/1984 |
| EP | 0 317 180 | 5/1989 |
| EP | 394956 | 10/1990 |
| EP | 415055 | 3/1991 |
| EP | 0 617 972 | 10/1994 |
| EP | 624635 | 11/1994 |
| EP | 1172083 | 1/2002 |
| EP | 1 285 670 | 2/2003 |
| GB | 2147002 | 5/1985 |
| JP | 57-82313 | 5/1982 |
| JP | 63-10731 | 1/1988 |
| JP | 63-203162 | 8/1988 |
| JP | 1-31714 | 2/1989 |
| JP | 2-193915 | 7/1990 |
| JP | 3-109327 | 5/1991 |
| JP | 4-504969 | 9/1992 |
| JP | 7-39748 | 2/1995 |
| JP | 8-12582 | 1/1996 |
| JP | 9-10295 | 1/1997 |
| JP | 9-143060 | 6/1997 |
| JP | 9-169655 | 6/1997 |
| JP | 10-295798 | 11/1998 |
| JP | 11-188054 | 7/1999 |

(Continued)

OTHER PUBLICATIONS

Burks,"Povidone-Iodine Solution in Wound Treatment." Physical Therapy 1998:78(2);212-218.*
Horkay et al., "Osmotic and SANS Observations on Sodium Polyacrylate Hydrogels in Physiological Salt Solutions." Macromolecules 2000:33;8329-8333.*

*Primary Examiner* — Walter Webb
(74) *Attorney, Agent, or Firm* — Wenderoth, Lind & Ponack, L.L.P.

(57) ABSTRACT

There is provided an external preparation for wounds which has novel usability in treating skin damages accompanied by a large amount of exudation such as bedsores, skin ulcers, and burns, and yet has such advantages as observed in conventional medicines having been employed in treating these wounds. The external preparation for wounds comprises a water-soluble polymer and a crosslinking agent, and has powdery/granular or ointment form. After absorbing an exudation, the preparation undergoes phase transition from a sol to a gel by the action of ingredient of the preparation, and thus exhibits actions of adsorbing and eliminating necrotic tissues, and protecting the wounded parts. Subsequently, it can continuously absorb the exudation. After being used, it can be easily separated substantially as a mass, thereby exhibiting high therapeutic effects and usability.

6 Claims, No Drawings

FOREIGN PATENT DOCUMENTS

| | | |
|---|---|---|
| JP | 2000-38342 | 2/2000 |
| JP | 2001-212170 | 8/2001 |
| WO | 85/02092 | 5/1985 |
| WO | 93/11751 | 6/1993 |
| WO | 95/24172 | 9/1995 |
| WO | WO98/58651 | * 12/1998 |
| WO | 99/09962 | 3/1999 |
| WO | 01/22907 | 4/2001 |

* cited by examiner

EXTERNAL PREPARATION FOR WOUNDS

TECHNICAL FIELD

The present invention relates to an external preparation for wounds for use in treatment and procedure of skin damages. More specifically, the external preparation is of powdery/granular or ointment form, and is capable of being into every hole and corner of wounded parts of complex configuration because of its powdery/granular or ointment form. Further, the external preparation is capable of adsorbing and eliminating necrotic tissues by turning to a gel while absorbing exudation, and promoting restoration of skin tissues by its sustained absorbability of the exudation after the gelation. Furthermore, the external preparation has a superior property of being easily separated substantially as a mass after its use.

BACKGROUND ART

In skin damages, particularly in bedsores extending all over the skin layers, serious skin ulcers, burns, or the like, intensive exudation observed and obstructs skin restoration. In view of this, it is significant to find a measure as to how effectively the exudation is drained and eliminated from the wounded parts in treating such skin damages. In old days, granulated sugar or white soft sugar, which are composed of sucrose, had been used to treat skin damages accompanying exudation.

The sucrose exhibits bacteriostatic action and granulation promoting action particularly in treating bedsores. The sucrose itself is effective in draining the exudation from the wounded parts. It is conceived that these properties of the sucrose may promote tissue restoration. Unlike patch-like protection materials, the sucrose can be into every hole and corner of the wounded parts having complexity in configuration because of its granular form.

Despite the above merit that the sucrose has the action of draining exudation, its absorbability of exudation is poor. Accordingly, it is more likely that the drained exudation may penetrate through the sucrose layer and ooze out of the gauze or the like, with the result that the clothing or the like may be smeared. Further, the oozing of the exudation out of the gauze or the like may not only make patients feel uncomfortable but also constitute a burden for caretakers because the caretakers must clean the peripheral areas of the wounds, the clothing or the like. Therefore, oozing of exudation causes a troublesome issue in actual care and treatment.

In view of the above, there is a demand for a novel preparation for treating wounds that can be into every hole and corner of wounded parts having complexity in configuration for protection, and has exudation absorbability.

Japanese Examined Patent Publication No. SHO 61-34829 recites such a preparation for wounds. The preparation contains a gel in the form of dry powder as an ingredient. The gel can absorb and hold the exudation therein. The preparation is convenient because the gel swells by absorbing the exudation, and the powder particles of the gel are rendered viscous and are bound to each other into a viscous material, which allows easy separation from the affected parts. Japanese Unexamined Patent Publication No. HEI 9-169655 discloses an external powder preparation for skin ulcers having a similar action as the preparation disclosed in Japanese Examined Patent Publication No. SHO 61-34829. The powder preparation contains not only a gel (water-swelling cellulose and binding agent) but also sugar and iodophors as ingredients. Therefore, the powder preparation not only exhibits exudation absorbability and usability, but also has preventive effect of invection of bacteria as well as wound-treating effects.

Despite the aforementioned various technical measures, there is a case that sufficient therapeutic effects are not obtainable in treating serious skin damages.

For instance, the conventional therapeutic preparation for wounds employs a water-insoluble gel material as an ingredient. With use of the conventional preparation, adhesiveness among the particles of the gel is increased as the gel material absorbs the exudation to swell. However, such a swelling does not provide firm binding among the particles, and fails to provide usability that the preparation is easily separated as a mass after the use. Particularly, in treating serious wounds which have a relatively great depth and complex configuration, the preparation is likely to be applied too deeply into the wounded parts, and the swollen particles may remain on the wounded parts, because it is difficult or impossible to make a mass having a sufficient strength by mere swelling of the gel in an attempt to increase adhesiveness among the particles. In the case where sugar, a bactericide, or the like is added to promote skin restoration on the wounded areas, the addition of such components may further obstruct the preparation from forming a mass. As a result, it is more likely that part of the preparation may remain on the wounded parts, because the swollen gel is split into parts in removing the mass from the wounded parts after the use of the preparation.

Japanese Examined Patent Publication No. SHO 61-34829 recites "in many cases, such a drawback can be completely eliminated by cleaning the wounded part, which is treated". However, such a cleaning is not desirable, considering daily tasks of caretakers and suffering of bedridden patients.

Eliminating necrotic tissues from the wounded parts is highly effective in treating serious wounds. However, existence of the gel material on the wounded parts from the initial stage of the treatment fails to form a mass having such strength as to adsorb and eliminate necrotic tissues after the use of the preparation.

Furthermore, if the conventional preparation is used in the form of an ointment in an attempt to increase usability in treatment, binding ability among the particles is further lowered, which makes it difficult to eliminate the mass of the preparation after the use. In other words, utilizing the conventional preparation as an ointment is very difficult.

As mentioned above, there is a demand for an external preparation for wounds whose use is highly convenient in actual on-site treatment, and which provides further therapeutic effects in treating serious bedsores, skin ulcers, burns, and the like.

An object of the present invention is to provide a powdery/granular external preparation for wounds to be applied to skin damages accompanying a large amount of an exudation, particularly serious bedsores or the like. The external preparation can be into every hole and corner of wounded parts having complexity in configuration, actively and sustainably lead drainage of the exudation from wounded parts to absorb the exudation without leakage to the outside, substantially form a mass of a gel to protect the wounded parts having such a strength as to adsorb necrotic tissues even in a condition that the other ingredient such as sugar or a bactericide is added, and can be easily separated along with a gauze or the like after the use of the preparation, adsorbing the necrotic tissues.

Use of an ointment containing the above powdery/granular external preparation for wounds as the inventive preparation is advantageous in that it is easy to apply the ointment to the wounded parts because the ointment has good spreadability, in addition to the above properties. Also, such an ointment is easily applied to a gauze or the like. Accordingly, another object of the present invention is to provide an ointment external preparation for treating wounds having high therapeutic effects and usability.

DISCLOSURE OF THE INVENTION

As a result of an intensive study and research regarding external preparations for wounds in order to solve the above problems, the inventors found that transforming a sol (un-cross-linked) polymer to a gel with use of an exudation on wounded parts gives the external preparation superior exudation absorbability. Further, as such an external preparation is transformed to the gel having adequate strength and the gel is substantially turned to a mass after the use, the external preparation can be easily eliminated after the use. As the result, the inventors accomplished the invention.

A powdery/granular external preparation of the present invention is for use in treatment and procedure of skin damages, characterized in comprising a water-soluble polymer of 2% or more (preferably 5% or more) and a crosslinking agent of from 0.01% to 20%, and the water-soluble polymer is in uncross-linked state.

The water-soluble polymer preferably contains acidic group in its structure. A preferred example of the acidic group is carboxylic group or sulfonic acid group. Preferably, the crosslinking agent is polyvalent metal salt. Particularly, a crosslinking agent containing aluminum is preferred. Because they make it easy to control the property of the gel after sol-to-gel transformation and particularly, and make it possible to form the gel having such strength as to eliminate necrotic tissues residing on wounded parts while entrapping the same.

Sodium polyacrylate is an optimum compound as the water-soluble polymer because its superiority as an ingredient of the inventive preparation has been verified, as will be described later in Examples.

Preferably, the preparation contains a bactericide of from 0.1% to 10%. A preferred example of the bactericide is an iodine-containing bactericidal agent because it can sterilize wounded parts and prevent infection by bacteria, and is superior as a therapeutic agent for wounds.

Preferably, the preparation contains sugars of from 5% to 70%. The sugars have enjoyed prestige as therapeutic preparations in treating wounds from old times, and have bacteriostatic action and granulation promoting action.

Preferably, the moisture content of the external preparation for wounds is 3% or less. An excessive content of moisture may cause the water-soluble polymer or the like to dissolve, thereby causing gelation of the preparation.

The ointment external preparation for wounds of the present invention comprises the aforementioned powdery/granular external preparation for wounds, and a fluidization agent. The ointment external preparation for wounds has superior spreadability, in addition to the effects resulting from the powdery/granular external preparation for wounds, and also provides superior usability as an external preparation for wounds.

Preferably, the fluidization agent is macrogol. Use of the macrogol is preferred because it enjoys prestige as an ingredient of the ointment.

A primary feature of the inventive external preparation for wounds resides in that the water-soluble polymer of the preparation is dissolved as the preparation absorbs the exudation in wounded areas, and simultaneously the polymer shows phase transition to a gel while being crosslinked by the crosslinking agent, although the preparation has a powdery/granular or ointment form before its use. The preparation can be into every hole and corner of wounded parts having complexity in configuration owing to the properties inherent to the powdery/granular or ointment preparation. The preparation makes it possible to adsorb and eliminate necrotic tissues on the wounded parts by forming a gel, and protect the wounded areas, with easy separation of the gel substantially as a mass after its use.

What is significant in the present invention is that since the inventive external preparation for wounds forms a gel having a sufficient strength, it exhibits the aforementioned effects as expected in the present invention by turning to the gel while absorbing the exudation, even in the form of an ointment, which is highly useful in actual on-site treatment.

Since the water-soluble polymer contained in the external preparation exhibits good absorbability even after phase transition from the sol material to the gel, the preparation can promote regeneration of tissues on the wounded areas by continuously absorbing the exudation.

In the following, preferred embodiments of the present invention that can exhibit these effects will be described in detail.

The term "water-soluble polymer" as used in the present invention means a pharmaceutically acceptable polymer for external use. The water-soluble polymer is in an uncross-linked state (sol state) before use, and has a powdery/granular form. The kind of the water-soluble polymer is not specifically limited, as long the polymer forms a gel by the existence of a liquid such as an exudation and a crosslinking agent. Examples of the water-soluble polymer include: compounds having carboxyl group in their structures such as polyacrylic acid, alginic acid, pectin, carmellose, starch-acrylic acid graft co-polymer and carboxyvinyl polymer; compounds having sulfonic acid group such as carageenan; compounds having a hydroxyl group such as polyvinyl alcohol, alginic acid, pectin, carmellose and carageenan; polysaccharides such as xanthan gum, gellan gum, alginic acid, pectin, carmellose and carageenan; proteins such as gelatin; salts of these compounds: and combination of at least two kinds thereof. In case of using a compound which forms a gel by the existence of polyvalent ions such as polyacrylic acid or alginic acid as a salt, it is preferable to use a monovalent metal salt such as sodium salt and potassium salt.

The term "gel" as used herein means a polymer and swollen material thereof which have three-dimensional network structure and are insoluble in all the possible solvents (see page 129, "Polymer Dictionary" new version edited by the Society of Polymer Science, et al., Japan published by Asakura Shoten). The term "sol-to-gel transformation" herein means that interaction is caused between particles (or molecules) constituting a sol, with the result that the sol turns to a gel which contains a medium and is solidified in its entirety (see page 255, the above "Polymer Dictionary"). Specifically, the water-soluble polymer as an ingredient of the inventive preparation is a compound which forms a gel by the action that the water soluble polymer in an uncross-linked state in its initial stage of use is dissolved in an exudation, and the molecules of the dissolved polymer components are crosslinked to each other by the crosslinking agent. In this sense, the water soluble polymer is a sol polymer in particle state before the polymer forms a three-dimensional network structure in which the molecules of the polymer are crosslinked to each other by the crosslinking agent. In some of the conventional technical documents, "gelation" means that a dry gel material having a three-dimensional network structure by nature turns to a water-insoluble viscous material by absorbing moisture to swell. However, according to the definition of the present invention, such a change of condition is not "gelation or gel formation (sol-to-gel transformation)".

The water soluble polymer in the present invention is first dissolved in exudation because of its water-soluble property, and binding between the respective molecules of the polymer is highly progressed by the crosslinking agent which is dissolved in the exudation. This is advantageous in substantially forming a mass of gel material having a high strength, as compared with the conventional preparation having water-insoluble gel material, which swells, by nature.

Preferably, the water soluble polymer in the gel state has high and continuous absorbability of exudation. Since bedridden patients suffering from bedsores feel great pain in exchange of the preparation for wounds, it is required to minimize the frequency of exchanging the preparation. In view of this, it is desirable that the exudation absorbability of the preparation is as high and continuous as possible. Such exudation absorbability can be controlled by selecting the kind of the water-soluble polymer.

It is essentially important that the content of the water-soluble polymer is 2% or more relative to the total content of the external preparation for wounds. If the content of the water-soluble polymer is less than 2%, the preparation does not cause gelation, with the result that exudation absorbability from the wounded parts is not sustained for a desirable period. In view of this, to allow the preparation to exhibit sufficient exudation absorbability, the content of the water-soluble polymer is preferably 10% or more, more preferably 20% or more, and furthermore preferably 30% or more, yet furthermore preferably 40% or more, still furthermore preferably 50% or more, and particularly preferably 60% or more. In case of using the external preparation for wounds as an ointment, the content of the water-soluble polymer relative to the total mass of the ointment is preferably 5% or more, more preferably 10% or more, and particularly preferably 15% or more. The upper limit of the content of the water-soluble polymer is not specifically limited. However, considering the balance with the other ingredients or other factor, the upper limit of the content of the water-soluble polymer is 95% or less, and more preferably 90% or less.

The term "crosslinking agent" as used herein means a pharmaceutically acceptable compound for external use. As long as the crosslinking agent exhibits sufficient solubility to the exudation, and is capable of forming a gel by crosslinking the sol-state water-soluble polymer, the kind of the crosslinking agent is not specifically limited. For instance, if the water-soluble polymer having carboxyl group or sulfonic acid group is used, a polyvalent metal salt is usable. If the water-soluble polymer having hydroxyl group is used, a boric acid (including its salt or borax), a dicarboxylic acid, dialdehyde, or the like is usable. Any crosslinking agent is usable, as far as it shows solubility by interaction of the exudation and a polyvalent alcohol or the like, which is a water-soluble polymer, even if such a crosslinking agent does not show sufficient solubility in the exudation alone.

It is preferable to use a polyvalent metal salt as the crosslinking agent, in view of the aspects that it is easy to obtain the polyvalent metal salt, the pharmaceutical behavior of the polyvalent metal salt has been well known, and safe use thereof has been verified. Examples of the polyvalent metal salts include: aluminum-containing crosslinking agents such as aluminum oxide, aluminum acetate, aluminum glycinate, aluminum lactate, potassium alum, dihydroxyaluminum allantoinate, sucrose octasulfate—aluminum complex, aluminum silicate hydrate and synthetic aluminum silicate; polyvalent metal chlorides such as magnesium chloride and calcium chloride; polyvalent metal bromides such as magnesium bromide and calcium bromide; polyvalent metal oxides such as calcium oxide and aluminum oxide; polyvalent metal salts of organic acid such as aluminum acetate, aluminum glycinate and aluminum lactate; polyvalent metal salts of silicates such as magnesium silicate, aluminum silicate hydrate, magnesium aluminosilicate, magnesiumaluminometasilicate and synthetic aluminum silicate; aluminum-and-magnesium-containing compounds such as synthetic hydrotalcite and hydrated alumina/magnesium; and combination of at least two kinds thereof.

It is necessary to set the content of the crosslinking agent, relative to the total content of the external preparation for wounds, at 0.01% or more (preferably 0.1% or more, more preferably 1% or more, and furthermore preferably 2% or more), and 20% or less (preferably 15% or less, and more preferably 10% or less). If the content of the crosslinking agent is less than 0.01%, sufficient crosslinkability is not obtainable after absorption of the exudation in the wounded parts, thereby making it difficult to eliminate necrotic tissues. On the other hand, if the content of the crosslinking agent exceeds 20%, it is more likely that the resultant gel material itself is too solid, with the result that water is dissociated therefrom, and sufficient exudation absorbability is not obtainable. In case of formulating an ointment external preparation for wounds according to the present invention, the more the crosslinking agent is added, the better it is preferable, in consideration of the contact of the crosslinlking agent with the water-soluble polymer.

Appropriate operations and effects of the present invention, namely, the advantages that the inventive external preparation has sufficient exudation absorbability before and after gel formation, makes it easy to separate the mass of the gel after the use of the preparation while adsorbing necrotic tissues after the gel formation, are obtained by optionally selecting or combining the water-soluble polymer, combining the water-soluble polymer with the crosslinking agent, selecting or combining the crosslinking agent, and appropriately adjusting the contents of these ingredients. For instance, a preferred combination of attaining relatively easy gel formation by exudation is a combination of water-soluble polymer having acidic group such as carboxyl group or sulfonic acid group in its structure, with polyvalent metal salt as crosslinking agent.

The water-soluble polymer and the crosslinking agent, as the ingredients of the inventive preparation, form a gel by interaction of these ingredients with the exudation while being dissolved in the exudation on the wounded parts. In this way, since these ingredients form the gel having a sufficient strength while entrapping the necrotic tissues in the wounded parts, removability of the necrotic tissues is remarkably high in the inventive preparation, as compared with the conventional therapeutic preparation having the gel material by nature in which the gel material swells by absorbing exudation.

It is possible to add a well-known pharmaceutical for treating wounds, to the inventive external preparation, in addition to the water-soluble polymer and the crosslinking agent. For instance, sugars having an action of discharging exudation, bacteriostatic action and granulation promoting action; bactericidal agents of preventing infection and proliferation of bacteria; enzymes of decomposing proteins or nucleic acids such as trypsin, bromelain, streptokinase, streptodornase, fibrinolysin and deoxyribonuclease; anti-inflammatory such as zinc oxide and azulene; granulation accelerators such as lysozyme chloride, tretinoin tocoferil, prostaglandin, bucladesin sodium, aluminum chlorohydroxy alcloxa (allantoinate), fibroblast growth factor (FGF), hepatocyte growth factor (HGF) may be added depending on the purpose of use. Alternatively, absorptive polymer beads may be added to assist water absorption.

The kind of the bactericide contained in the inventive preparation is not specifically limited, as long as the agent has a bactericidal action. However, it is essentially required that the bactericide is a pharmaceutically acceptable compound. Examples of the bactericide include sulfadiazine silver; iodione-based bactericide such as povidone iodine, iodine and salts of iodide ions; fradiomycin sulfate; acrinol; chlorhexidine; benzalkonium chloride; and benzetonium chloride. Among them, the iodine-based bactericidal agents are preferred, because they have a high antimicrobial action and chemical properties suitable for the antimicrobial action. Addition of potassium iodide along with the iodine makes it possible to allow the preparation to exhibit stability and water-solubility. Further, the water-soluble polymer, as the ingredient of the inventive preparation, can hold the iodine in a stable manner for a long term.

Examples of the sugars contained in the inventive preparation include sucrose such as refined sugar, granulated sugar, and white soft sugar, and sugars having therapeutic effects such as sorbitol, mannitol, fructose, glucose, xylitol, lactose, maltose, maltitol and trehalose. Among them, the sucrose such as granulated sugar and white soft sugar are preferably usable because of their particularly high therapeutic effects.

The content of the sugars preferably is from 5% to 70%. If the content of the sugars is less than 5%, sufficient therapeutic effects inherent to the sugars are not obtainable. On the other hand, if the content of the sugars exceeds 70%, it is impossible to form a gel having a sufficient strength. A further preferred range of the content of the sugars is from 10% to 60% inclusive.

Since the above additives do not have gel formability, they may hinder the external preparation from forming a mass of the gel after the exudation has been absorbed. However, since the inventive external preparation for wounds has superior gel formability, the preparation is capable of substantially forming a mass of the gel having such a strength as to be easily removable after its use and to adsorb and eliminate the necrotic tissues, even in case where the additives are added.

The inventive powdery/granular external preparation for wounds has plasticity because of its powdery/granular form, and can be contacted with every hole and corner of wounded parts having complexity in configuration to protect the wounded areas by phase transition to a gel at the respective wounded areas. Further, in case of using the powdery/granular external preparation as an ointment, it is easy to uniformly disperse the ingredients over the entirety of the ointment. It is preferable to set the moisture content of the preparation at 3% or lower in order to retain the powdery/granular state. An excessive addition of the moisture content above 3% may likely to deprive the preparation of plasticity, as the water-soluble polymer is dissolved and the crosslinking is progressed, thereby obstructing the preparation from exhibiting the properties inherent to the powdery/granular preparation. Further preferably, the moisture content of the preparation is 2% or less (furthermore preferably, 1% or less), considering long-term stability of the preparation.

The term powdery/granular state herein embraces the meaning of powdery state and granular state. The particle diameter of the preparation is not specifically limited, as far as the preparation is recognizable as powder or granule. However, it is essentially important that the particle diameter is sufficiently small so as to be contacted with every hole and corner of wounded parts having complexity in configuration.

There is proposed a manner of directly spraying the inventive powdery/granular preparation onto wounded areas, followed by covering the applied parts with a sterilized gauze or the like, as an example as to how the inventive powdery/granular external preparation for wounds is used. Covering the applied parts with the gauze or the like makes it possible to remove the inventive preparation that has turned to a gel, along with the gauze or the like while adsorbing necrotic tissues. In other words, the inventive external preparation for wounds provides extensive use in daily medical treatment because the external preparation after its use can be easily removed without contact with the applied parts with substantially no residues of the preparation on the applied parts, which eliminates cleaning operation.

The inventive preparation can be used as powdered medicine. The powdered medicine, however, may likely to be scattered during its use, with the result that it may smear the sheets, the clothing, skin or hands. In view of this, utilizing the inventive external preparation for wounds in the form of an ointment provides sophisticated and handy use in actual on-site treatment, while providing the properties inherent to the powdery/granular external preparation.

The inventive ointment external preparation for wounds can be produced by admixing a fluidization agent to the powdery/granular external preparation. The term "fluidization agent" herein means an agent that imparts fluidity to a powdery/granular material, and inhibits gel formation without dissolving either or both the water-soluble polymer and the crosslinking agent. The kind of the fluidization agent is not specifically limited, as far as the fluidization agent is a pharmaceutically acceptable compound, and has the above properties. Examples of the fluidization agent include macrogol, glycerin, butanediol, propyleneglycol, Vaseline, liquid paraffin and plastibase.

As an exemplified manner as to how the inventive ointment external preparation is used, there is proposed a manner of applying the preparation onto the wounded parts, followed by covering the applied parts with a gauze or the like, or alternatively, applying the preparation onto a sterilized gauze or the like, followed by covering the wounded parts with the gauze or the like. Applying the ointment having spreadability onto a gauze or the like is easy and useful, as compared with applying the powdery/granular preparation onto a gauze or the like. Further, the inventive ointment external preparation for wounds can be easily separated from the wounded parts along with the gauze or the like after the use, which lessens the burden of the caretakers.

In case of using the inventive external preparation for wounds on wounded parts with less exudation, there are proposed manners of cleaning the wounded parts with saline or the like and applying the preparation onto the wounded parts without wiping off, or alternatively, applying the preparation to the wounded parts, using a wet gauze. In case of using the ointment external preparation, the ointment may be immersed in water prior to its use to promote gel formation.

In addition to the above components, the inventive external preparation for wounds may include an excipient, pH adjustor (such as tartaric acid), buffer, surfactant, wetting agent, plasticizer, colorant, preservative, fragrance, stabilizer, or the like in a pharmaceutically acceptable amount according to needs.

BEST MODE FOR CARRYING OUT THE INVENTION

Next, the present invention will be described further in detail by way of Examples and Test Examples. The Examples and Test Examples do not limit the spirit and scope of the invention as defined by the claims appended hereto. The respective units of the blending quantities throughout the Examples and Comparative Examples is mass %.

Example 1

Preparation of Powdery/Granular External Preparations for Wounds

The powdery/granular external preparations for wounds of the present invention were prepared as powdered medicine each in the following blending quantity.

TABLE 1

| Ingredients | Preparation No. 1 | Preparation No. 2 | Preparation No. 3 |
|---|---|---|---|
| sodium polyacrylate | 30 | 20 | 30 |
| carmellose sodium | 30 | | |
| polyvinyl alcohol | | 20 | |
| carboxyvinyl polymer | | | 40 |
| aluminum lactate | 5 | 3 | 6 |
| white soft sugar | residue | residue | |
| popidon iodine | 1 | 1 | 1 |
| mannitol | | | residue |

Example 2

Preparation of Ointment External Preparations for Wounds

The ointment external preparations for wounds of the present invention were prepared each in the following blending quantity.

TABLE 2

| Ingredients | Preparation No. 4 | Preparation No. 5 |
|---|---|---|
| sodium polyacrylate | 14 | 10 |
| carmellose sodium | 10 | 10 |
| aluminum lactate | | 3 |
| magnesiu maluminometasilicate | 1 | |
| synthetic hydrotalcite | 0.1 | |
| white soft sugar | 10 | |
| potassium iodide | 1 | 1 |
| malic acid | 1.4 | |
| tartaric acid | 2 | 2 |
| iodine | 1 | 1 |
| macrogol | residue | residue |

Comparative Example 1

As a comparative example, powdery/granular and ointment external preparations for wounds were prepared each in the following blending quantity.

TABLE 3

| Ingredients | Preparation No. 6 | Preparation No. 7 |
|---|---|---|
| white soft sugar | residue | 10 |
| potassium iodide | | 1 |
| popidon iodine | 1 | |
| iodine | | 1 |
| concentrated glycerin | | 30 |
| macrogol | | residue |

Comparative Example 2

As a comparative example, an external preparation, which is gel material by nature, was prepared by the formulation recited in Japanese Examined Patent Publication No. 61-34829.

TABLE 4

| Ingredients | Preparation No. 8 |
|---|---|
| acrylamide | 3.2 g |
| bis acriylamide | 82 mg |
| agarose | 2 g |

A gel plate of 3 mm in thickness was formed by blending the ingredients. After washing, the gel plate was dried at 50° C. for 24 hours in a drying vessel. The dried substance was pulverized and sieved. Thus, a powdery external preparation with 0.2 mm or less in particle diameter was prepared.

Test Example 1

50 g of Preparations No. 1 and No. 4 in Examples 1 and 2 each was charged in a laminated tube, and the laminated tubes were put in a stabilization tester kept at 40° C. with 75% in humidity to evaluate the content of iodine, as an effective ingredient of the preparation, after 1 month and 2 months. Measurement of the iodine content was carried out by the determination method recited in C-2606 in "Japanese Pharmacopoeia XIII" published by Hirokawa Shoten (1996). Further, external appearance of the preparation after 2 months was observed. The results of the measurement and observation are shown in Table 5, in which the content of iodine residue relative to the iodine content at charging (100%) is represented as %.

TABLE 5

| | Effective residue iodine content (%) | | External |
|---|---|---|---|
| | 1 month after | 2 month after | appearance |
| Preparation No. 1 | 99.2 | 96.3 | no change |
| Preparation No.4 | 97.3 | 95.5 | no change |

As is obvious from Table 5, no change was observed with respect to external appearance of Preparations No. 1 and No. 4 in 2 months after the charging, with the residue iodine content as the effective ingredient of 95% or more. The test results reveal that the inventive external preparation can stably retain the iodine for a long term, irrespective of the form of the preparation as to whether the preparation is powder or ointment.

Test Example 2

Tests were run in which Preparations No. 1 and No. 4 as the inventive external preparations, and Preparations Nos. 6 through 8 as comparative examples each in an appropriate quantity was applied to a lump of pork, followed by covering the applied parts with gauzes. After the pork was left for one day at room temperature, the gauzes were removed to examine how easily the gauzes were removable from the applied parts, as well as observing the conditions of the preparation. The test results are as shown in Table 6.

TABLE 6

|  | Removability | Condition |
| --- | --- | --- |
| Preparation No. 1 | ○ | ○ |
| Preparation No. 4 | ○ | ○ |
| Preparation No. 6 | X | X |
| Preparation No. 7 | X | X |
| Preparation No. 8 | X | — |

In Table 6, the middle column shows removability of the gauze: ○ represents that the preparation was easily removed along with the gauze, and X represents that the preparation could not be easily removed along with the gauze. The right column shows the condition of the preparation: ○ represents that the preparation formed a gel by absorbing the exudation, and X represents that the preparation did not form a gel.

The test results reveal that the inventive external preparations (namely, Preparations No. 1 and No. 4) formed gels, after having been applied and left for one day, owing to the exudation discharging and absorbing actions, with the result that the gels were easily removable along with the gauzes.

On the other hand, Preparations No. 6 and No. 7 as comparative examples failed to sustain the exudation, although they showed exudation discharging action, with the result that the exudation was oozed out of the gauzes. The test results reveal that use of Preparation No. 6 and No. 7 results in oozing of the exudation out of the gauzes, which may smear bed sheets or the like, and resultantly make the patients feel uncomfortable.

Preparation No. 8 as a comparative example absorbed the exudation and swelled because the preparation is composed of gel material by nature. However, the preparation failed to form a substantial mass of the gel, only form an aggregate of particles. Since the bonding between the particles is weak, the preparation could not be removed as a mass along with the gauze.

The test results reveal that the inventive external preparation enables to form a gel by absorbing an exudation to protect the wounded parts, irrespective of the form of the preparation as to whether the preparation is powder or ointment, and its usability is improved because it can be easily removed after its use.

Test Example 3

Skin-damaged rat models were prepared by shaving the hair on the back of each rat and making heat burn of 1 cm in diameter on the back. Preparations No. 1 and No. 4 as the inventive external preparations, and Preparation Nos. 6 through 8 as comparative examples each in the quantity of 500 mg was applied to the burnt parts of the rat models. The applied parts were covered with gauzes, and left for one day. During the test, the rats had their movement restrained by hampers. After one day, the gauzes were removed to observe how easily the gauzes were removable from the applied parts, as well as observing the condition of the preparation. The test results are as shown in Table 7.

TABLE 7

|  | Removability | Condition |
| --- | --- | --- |
| Preparation No. 1 | ○ | ○ |
| Preparation No. 4 | ○ | ○ |
| Preparation No. 6 | X | X |
| Preparation No. 7 | X | X |
| Preparation No. 8 | X | — |

The symbols in Table 7 have the same meaning as defined in Table 5.

Similarly to the test results in Test Example 2, the test results reveal that the inventive external preparations each formed a gel by discharging and absorbing exudation, thus providing high therapeutic effects and usability, whereas the comparative external preparations each showed that the exudation was oozed out of the gauze. Preparation No. 8 showed substantially the same result as that in Test Example 2, namely, a substantial mass of a gel was not formed.

Thus, the test results clarify that the inventive external preparation for wounds enables to form a gel by absorbing an exudation to protect the wounded parts in actual on-site treatment, and the gel is easily removable after the therapeutic application.

EXPLOITATION IN INDUSTRY

The inventive external preparation for wounds is contacted with every hole and corner of wounded parts having complexity in configuration over its entirety because of its powdery/granular or ointment form, exhibits superior exudation absorbability in possible respective wounded areas, and forms a gel after the exudation has been absorbed. The gel makes it possible to protect the wounded areas. Further, since the preparation has sustainability in absorbing the exudation after gel formation, the exchange frequency of the preparation can be reduced, which relieves burden of the patients. Further, since the external preparation after the gelation has a sufficient strength, it can securely adsorb and eliminate necrotic tissues. The gel is easily removable as a substantial mass after the use of the preparation, even if a therapeutic agent such as sugars and a bactericidal agent, which does not have gel formability, is added. Further, the inventive ointment external preparation for wounds provides high usability in actual on-site treatment of skin damages.

Thus, since the external preparation and the ointment according to the present invention have novel properties such as usability that has not been available in the conventional art, they are effective in treating skin damages such as severe bedsores, skin ulcers and burns.

The invention claimed is:

1. An ointment external preparation for wounds for use in treatment of skin damages, comprising
a sodium polyacrylate in an uncross-linked state of 2% or more based on the weight of the preparation, which is in sol state before use, and then simultaneously shows phase transition to gel after the preparation absorbs exudation in a wounded area of the skin,
a crosslinking agent in an amount of from 0.01% to 20% based on the weight of the preparation, which is a polyvalent metal salt selected from the group consisting of an aluminum-containing cross-linking agent, a polyvalent metal chloride, a polyvalent metal bromide, a polyvalent metal oxide, a polyvalent metal salt of an organic acid, a polyvalent metal salt of a silicate, an aluminum-and-magnesium-containing compound, and a combination of at least two kinds thereof, an iodine-based bactericidal agent in an amount of from 0.1% to 10% based on the weight of the preparation, which is povidone iodine or iodine, a fluidization agent, and a sugar in an amount of from 5% to 70% based on the weight of the preparation, which is sucrose or a sugar having a therapeutic effect, wherein the sucrose is selected from the group consisting of refined sugar, granulated sugar and white soft sugar, and the sugar having a therapeutic effect selected from the group consisting of sorbitol, mannitol, fructose, glucose, xylitol, lactose, maltose, maltitol and trehalose, wherein the moisture content of the preparation is 3% or less based on the weight of the preparation, and the preparation has an ointment form before its use and protects the wound, by transformation from a sol to a gel during use, with easy separation of the gel substantially as a mass after its use.

2. The preparation according to claim 1, wherein the content of the sodium polyacrylate is 5% or more based on the weight of the preparation.

3. The preparation according to claim 1, wherein the polyvalent metal salt is aluminum-containing crosslinking agent.

4. The preparation according to claim 1, wherein the fluidization agent is polyethylene glycol.

5. An ointment external preparation for wounds for use in treatment of skin damages, comprising a sodium polyacrylate in an uncross-linked state of 2% or more based on the weight of the preparation, an aluminum-containing crosslinking agent in an amount of from 0.01% to 20% based on the weight of the preparation, a sucrose in an amount of from 5% to 70% based on the weight of the preparation, an iodine in an amount of from 0.1% to 10% based on the weight of the preparation, and polyethylene glycol, wherein the moisture content of the preparation is 3% or less based on the weight of the preparation, and the preparation has an ointment form before its use and protects the wound, by transformation from a sol to a gel during use, with easy separation of the gel substantially as a mass after its use.

6. The preparation according to claim 1, wherein the sugar is granulated sugar or white soft sugar.

* * * * *

UNITED STATES PATENT AND TRADEMARK OFFICE
CERTIFICATE OF CORRECTION

| | | |
|---|---|---|
| PATENT NO. | : 8,323,693 B2 | Page 1 of 1 |
| APPLICATION NO. | : 10/507522 | |
| DATED | : December 4, 2012 | |
| INVENTOR(S) | : Hamamoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1251 days.

Signed and Sealed this
Twenty-third Day of September, 2014

Michelle K. Lee
*Deputy Director of the United States Patent and Trademark Office*